United States Patent
Winther

(10) Patent No.: US 7,167,736 B2
(45) Date of Patent: Jan. 23, 2007

(54) NON-INVASIVE MEASUREMENT SYSTEM AND METHOD FOR MEASURING THE CONCENTRATION OF AN OPTICALLY-ACTIVE SUBSTANCE

(75) Inventor: Dale E. Winther, La Crescenta, CA (US)

(73) Assignee: Q Step Technologies, Inc., San Ramon, CA (US)

( * ) Notice: Subject to any disclaimer, the term of this patent is extended or adjusted under 35 U.S.C. 154(b) by 53 days.

(21) Appl. No.: 10/981,181

(22) Filed: Nov. 4, 2004

(65) Prior Publication Data

US 2006/0094942 A1     May 4, 2006

(51) Int. Cl.
*A61B 5/00*     (2006.01)
(52) U.S. Cl. ...................... 600/319; 600/318
(58) Field of Classification Search ................ 600/316, 600/317, 318, 319, 321, 323
See application file for complete search history.

(56) References Cited

U.S. PATENT DOCUMENTS

| | | | |
|---|---|---|---|
| 3,533,683 A | 10/1970 | Stark et al. ..................... 351/1 |
| 3,958,560 A | 5/1976 | March | |
| 4,641,349 A | 2/1987 | Flom et al. ..................... 382/2 |
| 5,291,560 A | 3/1994 | Daugman ....................... 382/2 |
| 5,432,866 A | 7/1995 | Sakamoto .................... 382/128 |
| 5,433,197 A | 7/1995 | Stark | |
| 5,471,542 A | 11/1995 | Ragland ...................... 382/128 |
| 5,572,596 A | 11/1996 | Wildes et al. ............... 382/117 |
| 5,713,353 A | 2/1998 | Castano | |
| 6,305,804 B1 | 10/2001 | Rice et al. ................... 351/221 |
| 6,477,394 B1 | 11/2002 | Rice et al. .................. 600/318 |
| 6,704,588 B1 * | 3/2004 | Ansari et al. ............... 600/319 |
| 6,853,854 B1 * | 2/2005 | Proniewicz et al. ........ 600/319 |

* cited by examiner

*Primary Examiner*—Eric Winakur
*Assistant Examiner*—Etsub Berhanu
(74) *Attorney, Agent, or Firm*—Jeffer Mangels Butler, et al.

(57) ABSTRACT

A method and system for non-invasively measuring the concentration of an optically-active substance in a subject are provided. The system includes a light source adapted to transmit light towards a subject or object having a concentration of an optically-active substance, a polarizer positioned between the light source and the subject, an image capturing device, and a processor. The image capturing device is positioned to receive light reflected from the subject and create a measured image therefrom. The measured image defines measured light intensity data. The processor is configured to calculate a concentration of the optically-active substance based on a selected portion of the measured light intensity data.

109 Claims, 5 Drawing Sheets

NON-INVASIVE MEASUREMENT SYSTEM AND METHOD FOR MEASURING THE CONCENTRATION OF AN OPTICALLY-ACTIVE SUBSTANCE

FIELD OF THE INVENTION

The present invention relates to a method and system for non-invasively measuring the concentration of an optically-active substance, in particular, the concentration of glucose in the bloodstream of a human.

BACKGROUND OF THE INVENTION

In certain instances, it is necessary to measure the concentration of particular substances in a person's bloodstream. Commonly used test procedures for measuring such concentrations are invasive, requiring the drawing of blood. This can be particularly unpleasant for individuals who need to obtain concentration measurements at frequent intervals. For example, diabetic patients need to monitor the levels of glucose in their bloodstream and are required to undergo such invasive measurement procedures on a daily basis, often several times a day. Typically, the measuring is done through a finger prick to draw blood, which is placed on a test strip that is then inserted into a glucose monitoring device.

To avoid the problems of invasive testing, non-invasive methods of measuring the concentration of blood stream components of interest, such as glucose, have been developed. Glucose and certain other compounds are known as "optically-active" compounds. As used herein, the term "optically-active" refers to those compounds that rotate polarized light when it is passed through solutions containing the compounds. Optical activity is also associated with isomers that are identical in chemical formula and structure, but whose atoms differ in spatial orientation such that members of the pairs are mirror images of one another. If both members of an optically-active pair of isomers are present in equal proportions in a mixture, the mixture is called "racemic," and it will not exhibit a net rotation of polarized light, as the rotary effects of each isomer will cancel each other. However, as is known to those skilled in the art, in mammals, glucose and certain other optically active substances are only present in the form of one of their optically-active isomers, thereby avoiding the rotary cancellation caused by racemic mixtures.

It is desirable to exploit the optical activity of optically active substances such as glucose as a means of non-invasively measuring their concentrations in humans. The rotation of plane polarized light is known to be proportional to the concentration of an optically-active substance in a solution through which the light passes, according to the following relationship:

$$\alpha = [\alpha]_D [C] l$$

wherein C is the concentration of the optically-active substance, l is the optical path length (i.e., the length of fluid through which the plane polarized light passes) and $[\alpha]_D$ is the specific rotation, a parameter specific to the optically-active substance which varies with temperature of the solution and the wavelength of light used.

One location that is suitable for performing non-invasive glucose measurements is the aqueous humor of the eye. The concentration of glucose in the aqueous humor directly relates to the concentration of glucose in the bloodstream. However, the relationship between the concentration of glucose in the aqueous humor and the rotation of polarized light transmitted through the aqueous humor is difficult to use for purposes of determining the concentration of glucose in the bloodstream. In part, this difficulty stems from the fact that accurately measuring the optical path length (l) is difficult in a structure having a geometry as complex as that of an eye. In addition, known techniques for measuring the rotation angle of plane polarized light are difficult to reliably implement outside of a laboratory setting, in particular a setting in which such non-invasive testing will be performed by the patient or by a technician. As a result, a need has developed for a method and system that address the foregoing problems.

SUMMARY OF THE PREFERRED EMBODIMENTS

In accordance with one aspect of the present invention, an apparatus is provided which comprises a light source adapted to transmit light towards an object containing a solution of an optically-active substance. The apparatus further comprises a polarizer, a first image capturing device and a processor. The polarizer is positioned between the light source and the object. The first image capturing device is positioned to receive a portion of light reflected from the object and adapted to create a measured image therefrom. The measured image defines measured light intensity data. The processor is configured to calculate a concentration of the optically-active substance based on a selected portion of the measured light intensity data.

The optically-active substance is preferably glucose. In a preferred embodiment, the apparatus comprises a housing, wherein the light source, polarizer, first image capturing device and processor are contained in the housing. More preferably, the apparatus is portable, and it is especially preferred that the apparatus is a hand-held device. In preferred embodiments, the object is a human eye having an iris and the measured image comprises a measured image of the iris.

In accordance with another preferred embodiment, a database is provided which comprises predetermined concentration data for the optically-active substance and predetermined light intensity data. The processor is configured to calculate a concentration of the optically-active substance based on the selected portion of measured light intensity data, a selected portion of predetermined concentration data, and a selected portion of predetermined light intensity data.

In accordance with other preferred embodiments, the object is a human eye having an iris and the polarizer is positioned to transmit light from the light source towards the iris such that the transmitted light contacts the iris at one or more angles of incidence, thereby creating the portion of light reflected from the object. It is especially preferred that one or more of the angles of incidence is sufficient to cause polarization.

In accordance with another aspect of the present invention, a method of calculating a concentration of an optically-active substance in an object containing a solution of the optically-active substance is provided. The method comprises providing at least one measured image of the object, each said measured image defining an array of measured intensities of light reflected from the object. The method further comprises calculating at least one ratio of measured intensities of light reflected from the object and calculating a concentration of the optically active substance based on the at least one measured ratio of light intensities. The object is preferably a human eye having an iris.

In a preferred embodiment, the step of calculating a concentration of an optically-active substance further comprises defining a plurality of calculation spaces in the measured image and calculating a calculation space ratio in each calculation space. The calculation spaces preferably comprise first and second regions, which more preferably, form an "L-shape."

In still other preferred embodiments, the method comprises providing a plurality of predetermined images of a reference object, each said predetermined image corresponding to a known concentration of the optically active substance, defining an array of predetermined intensities of light reflected from the object, and calculating at least one predetermined ratio of intensities within each said array of predetermined intensities. The concentration of the optically-active substance is calculated based on the at least one ratio of measured intensities and the at least one ratio of predetermined ratio of intensities within each said array of predetermined intensities of light reflected from the reference object.

In further preferred embodiments, the step of calculating at least one predetermined light intensity ratio within each array of predetermined intensities of light reflected from the reference object comprises defining at least one predetermined calculation space in each predetermined image and calculating a predetermined calculation space ratio in each predetermined calculation space, wherein the at least one predetermined light intensity ratio comprises at least one of the predetermined calculation space ratios.

In other preferred embodiments, the method comprises generating an offset error array. In additional preferred embodiments, the method comprises generating a minimum offset error array.

In accordance with another aspect of the present invention, a method of calculating a concentration of an optically-active substance in an object containing a solution of the optically-active substance is provided. The method comprises providing a measured image of the object. The measured image defines an array of measured intensities of light reflected from the object. The measured image is rotated to a plurality of rotational positions, thereby generating a plurality of rotated measured intensities of light reflected from the object. A concentration of the optically-active substance is calculated based on the measured intensities of light reflected from the object and the rotated measured intensities of light reflected from the object.

In accordance with an additional aspect of the present invention, a method of calculating a concentration of an optically-active substance in an object containing a solution of the substance is provided. The object includes a plurality of object regions. The method comprises providing a plurality of measured intensity values of light reflected from the object, wherein each measured intensity value corresponds to one of the object regions. A plurality of predetermined intensities of light reflected from a reference object containing a solution of the substance is also provided. The reference object includes a plurality of reference object regions, and each predetermined light intensity corresponds to one of the reference object regions and to a known concentration of the optically-active substance. A portion of the plurality of predetermined intensities of light reflected from the reference object is selected. A concentration of the optically-active substance is calculated based on one or more of the measured intensities of light reflected from the object and the selected portion of the plurality of predetermined intensities of light reflected from the object. In a preferred embodiment, the step of selecting a portion of the plurality of predetermined intensities of light reflected from the reference object is based on one or more statistical confidence parameters.

In accordance with another aspect of the present invention, a method of calculating the concentration of an optically-active substance in an object containing a solution of the substance is provided. The method comprises providing a measured image of the object, wherein the measured image defines measured light intensity data. A plurality of predetermined images of a reference object containing a solution of the optically-active substance are provided. Each predetermined image corresponds to a known concentration of the optically-active substance. The plurality of predetermined images define an array of predetermined light intensity data. The plurality of predetermined light intensity data defines a plurality of subarrays of predetermined light intensity data. The method further comprises rotating the measured image to a plurality of rotational positions, thereby generating rotated light intensity data, and selecting one of the subarrays. The concentration of the optically-active substance in the object is calculated based on the measured light intensity data, the rotated light intensity data, and the selected subarray of the predetermined light intensity data.

In accordance with another aspect of the present invention, a computer readable medium comprising instructions for calculating the concentration of an optically-active substance in an object containing a solution of the substance is provided. The method comprises receiving a measured image of the object which defines measured light intensity data.

A plurality of predetermined images of a reference object containing a solution of the optically-active substance is received. Each of the images corresponds to a known concentration of the optically-active substance, the plurality of predetermined images defines an array of predetermined light intensity data, and the array further defines a plurality of subarrays of predetermined light intensity data. The measured image is rotated to a plurality of rotational positions to generate rotated light intensity data. One of the subarrays of predetermined light intensity data is selected, and the concentration of the optically-active substance in the object is calculated based on the measured light intensity data, rotated light intensity data and the selected subarray of predetermined light intensity data.

BRIEF DESCRIPTION OF THE DRAWINGS

The invention may be more readily understood by referring to the accompanying drawings in which.

DETAILED DESCRIPTION OF THE EMBODIMENTS

The present invention relates to the surprising discovery that glucose levels in the bloodstream of a human subject can be correlated to ratios of intensities of light reflected from various regions of the iris of a human eye. In contrast, it has been found that very large changes in glucose concentration produce a relatively small degree of rotation of polarized light when it is passed through a glucose containing solution, such as the aqueous humor of a human eye. Thus, the relationship between concentration levels and polarized light rotation has proven unsatisfactory for reliably predicting glucose levels, particularly outside of the laboratory setting. However, it has been discovered that using ratios of intensities of light from the iris avoids this insensitivity problem.

Figure 1:
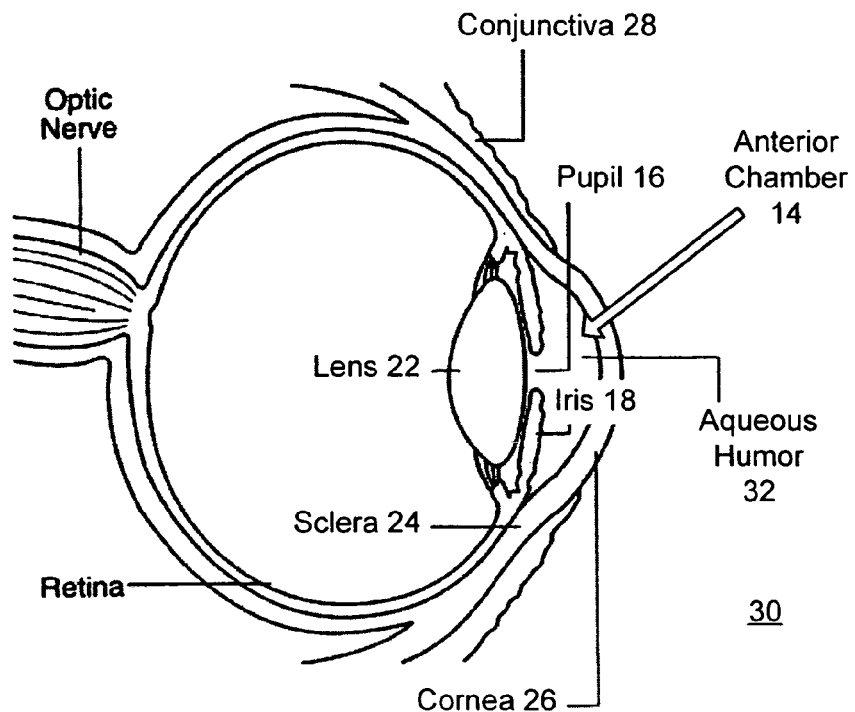
FIG. 1 is an illustration of an eye used to describe a method for measuring the concentration of an optically-active substance in accordance with a preferred embodiment of the present invention.

FIG. 1 is an illustration of an eye 30 of a subject used in the description of the various embodiments of the present invention. Eye 30 includes an anterior chamber 14 defined by a lens 22 and a cornea 26 that is filled with a fluid referred to as the aqueous humor 32. Eye 30 also has an iris 18 having a central aperture that defines a pupil 16. Iris 18 is surrounded by sclera 24 (i.e., the "whites" of the eye). Conjunctiva 28 covers upper and lower parts of sclera 24.

Figure 2:
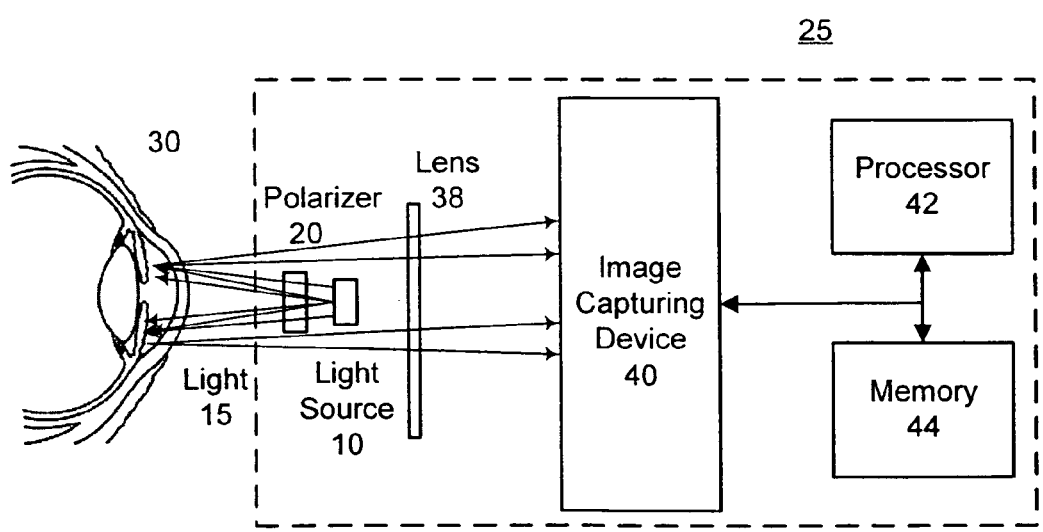
FIG. 2 is a depiction of a system for measuring the concentration of an optically-active substance in accordance with a preferred embodiment of the present invention.

Referring to FIG. 2, a system for measuring the concentration of an optically-active substance is provided. The system comprises a light source 10 which is adapted to transmit light 15 towards the iris of an eye 30 of a subject having a concentration of the optically-active substance in his or her bloodstream. Light source 10 is preferably placed in front of pupil 16 and is preferably a light emitting diode ("LED") or combination of light emitting diodes, each of which emits light at a different wavelength. For example, the following wavelengths can be used: 470 nm (blue), 525 nm (green), 625 nm (red), and 940 nm (near infrared). When only one wavelength is used, near infrared is preferred. When multiple wavelengths are used, blue, green, red and near infrared are preferred.

Lying in front of the iris 18 in eye 30 is the aqueous humor 32, which contains levels of solubilized glucose. Polarizer 20 is preferably positioned in-line with light source 10 and pupil 16 and between light source 10 and eye 30, such that light 15 passes through the polarizer 20 en route to eye 30. As a result, the light reaching the eye 30 is polarized. An image capturing device 40 is positioned to receive light reflected from eye 30. Preferably, the image capturing device 40 is a charge coupled device ("CCD"), such as the CV-M50 IR CCD manufactured by JAI Corporation of Japan, or another known image capturing device adapted to create an image from the light reflected from eye 30. A CCD has an array of light intensity detection locations called pixels. Thus, when light is received by the CCD, an array of intensity measurements is created. The array structure of a CCD enables it to obtain an image of the iris by measuring the intensity of light reflected from it.

To increase imaging efficiency, lens 38 is preferably provided and is positioned between light source 10 and image capturing device 40 at a distance of from about 1 mm to about 5 mm from light source 10 and at a distance of from about 15 mm to about 30 mm from image capturing device 40. In a preferred embodiment, lens 38 is a 25 mm lens with an F of 1.4. The position of lens 38 with respect to image capturing device 40 can preferably be adjusted to improve image focus.

Preferably, the light source 10 and polarizer 20 are positioned in-line with one another and with pupil 16. Although they may comprise separate components which are spaced apart from one another, more preferably, polarizer 20 and light source 10 form an integral unit and are not separated. Light source 10 is preferably placed at a distance of about 15 mm to about 30 mm from eye 30, with a distance of 20 mm being especially preferred.

Polarizer 20, light source 10, image capturing device 40, processor 42 and memory 44 can optionally be provided in a unitary housing (not shown), and more preferably, in the form of a portable, hand-held unit. The components of system 25 can also be separately connected without the use of a unitary housing. Also, two or more of the components can be combined in a single housing and then separately connected to or used with the remaining components.

According to the embodiment depicted in FIG. 2, the light source 10 and polarizer 20 are positioned such that light strikes the iris of the eye 30 at one or more angles of incidence. At least a portion of the light strikes the iris at an angle that is sufficient to polarize some of the light that is reflected towards image capturing device 40. Without limiting the scope of the invention in any way, it is theorized that owing to the curvature of the eye, the polarized light strikes the iris at a number of different angles of incidence, producing a scattering effect. As will be appreciated by those skilled in the art, when light strikes a surface, there is an angle of incidence called Brewster's angle at which the reflection coefficient becomes zero for the component of the light which is parallel to the incident surface. As a result, light reflected at Brewster's angle is polarized with its plane of vibration at right angles to the plane of incidence. Thus, it is theorized that at least a portion of the light striking the iris is polarized a second time (the first time being caused by polarizer 20) due to the effects of scattering and/or Brewster's reflection.

Again, without limiting the scope of the invention in any way, as a result of the foregoing dual polarization effect, it is theorized that the intensity of light reflected from the iris can be used as an indirect measure of the degree to which the plane of the polarized light is rotated by glucose contained within the anterior portion of the eye.

As depicted in FIG. 2, the image capturing device 40 is optionally connected to a processor 42, which is configured to calculate a glucose concentration, as described in greater detail below.

Construction of a Pattern Match Table

The system of FIG. 2 also includes a memory 44 that is operatively coupled to processor 42 and which contains predetermined glucose concentration data and predetermined light intensity data. Memory 44 preferably includes a pattern-match table of predetermined light intensity data versus known concentrations of glucose. In one embodiment, a pattern match table is generated for each subject who then uses it to predict his or her glucose concentration.

Figure 4:
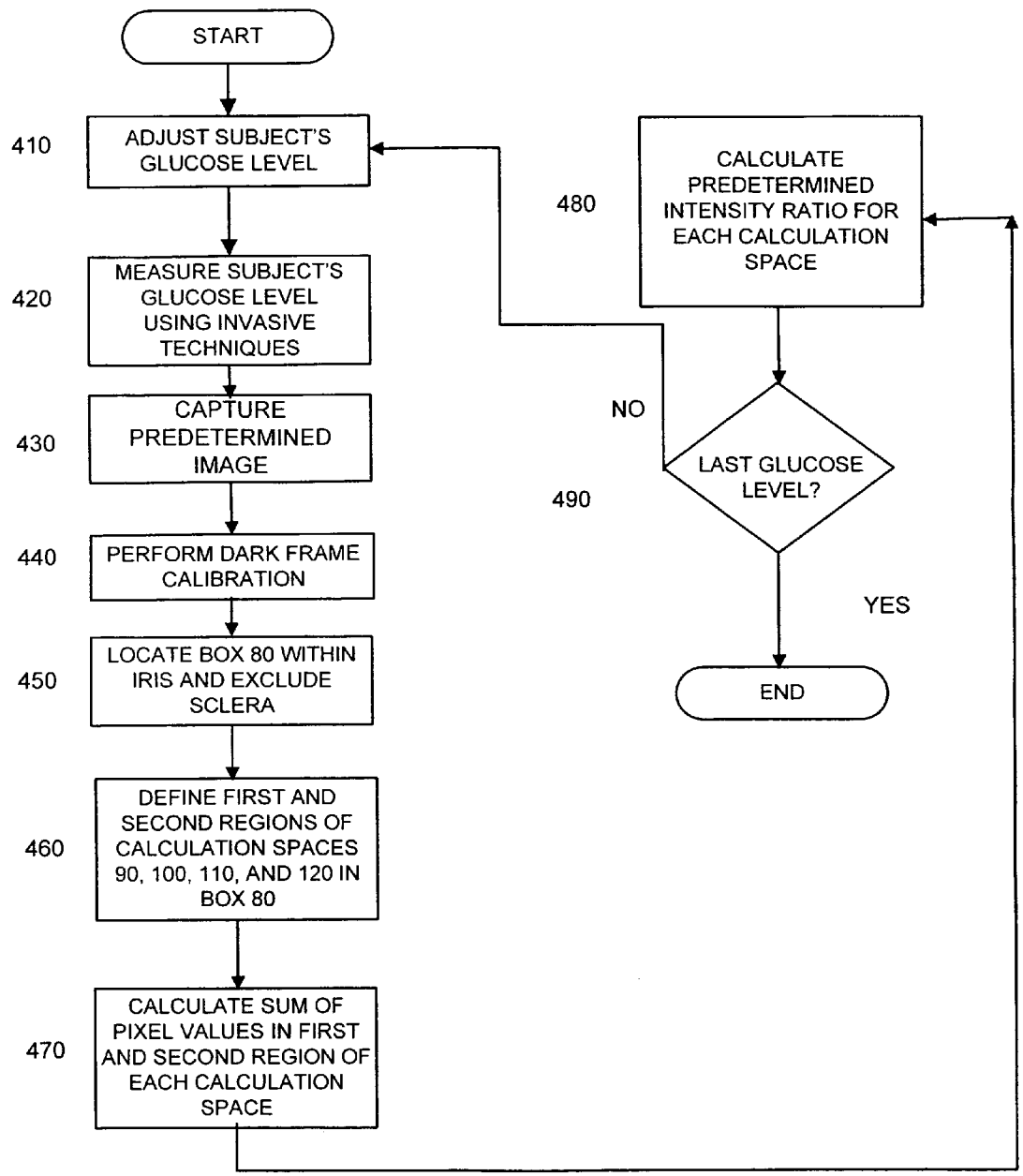
FIG. 4 is a flow chart depicting a method for generating predetermined light intensity data and predetermined concentration data in accordance with a preferred embodiment of the present invention.

FIG. 4 is a flow chart depicting a preferred embodiment of a method for generating a pattern match table. In step 410, glucose is supplied to the subject to adjust his or her glucose concentration. The glucose can be supplied, for example, by having the subject ingest glucola of fruit juice. After waiting for a period of time, preferably ten minutes, for the glucose to enter the bloodstream, the concentration of glucose in the subject's bloodstream is measured in step 420 using known invasive techniques.

Once the known concentration is established, light from light source 10 is directed towards eye 30 through polarizer 20. In step 430, light reflected from eye 30 is received by image capturing device 40, and a predetermined image is captured. Images generated as part of creating the pattern match table will be referred to herein as "predetermined images" to distinguish them from those images that are generated for the purpose of measuring an unknown concentration of glucose or other optically-active substance. Images obtained at unknown concentrations will be referred to herein as "measured images."

In step 430, light source 10, polarizer 20 and image capturing device 40 are preferably positioned such that a certain amount of light which strikes the iris of eye 30 experiences secondary polarization and is subsequently detected by image capturing device 40. Light source 10 is preferably integral with polarizer 20 and is placed at a distance of from about 15 mm to about 30 mm from eye 30, with a distance of 20 mm being especially preferred. Light source 10 and polarizer 20 are preferably placed in front of pupil 16. Lens 38 is preferably positioned in-line with light source 10, polarizer 20 and pupil 16 at a distance of from about 1 mm to about 5 mm from light source 10. Image capturing device 40 is preferably positioned in-line with light source 10, polarizer 20, lens 38 and pupil 16 at a distance of from about 15 mm to about 30 mm from lens 38.

Image capturing device 40 captures an image of the iris of eye 30 by measuring the intensity of light received at the various intensity measuring locations in the device, such as at the pixel locations in a CCD. As a result, an image of the iris is created. The image comprises the array of intensity measurements generated by the image capturing device 40. Preferably, the image is generated using a single wavelength of light 15. If multiple wavelengths of light are used, as will be described later, they are preferably used to generate a series of different images, each based on a single wavelength.

Because the pupil 16 of eye 30 lies within the iris 18, the image of the iris 18 will also include a pupil image lying within it. However, the pupil is not a structure in the eye, but rather, is an aperture defined by the inner perimeter of the iris. Thus, the pupil image will be substantially darker than the iris image due to the fact that relatively little light is transmitted into and reflected out of the pupil region. As explained further below, however, the pupil image is preferably not used to calculate the optically-active substance concentration.

Figure 3:
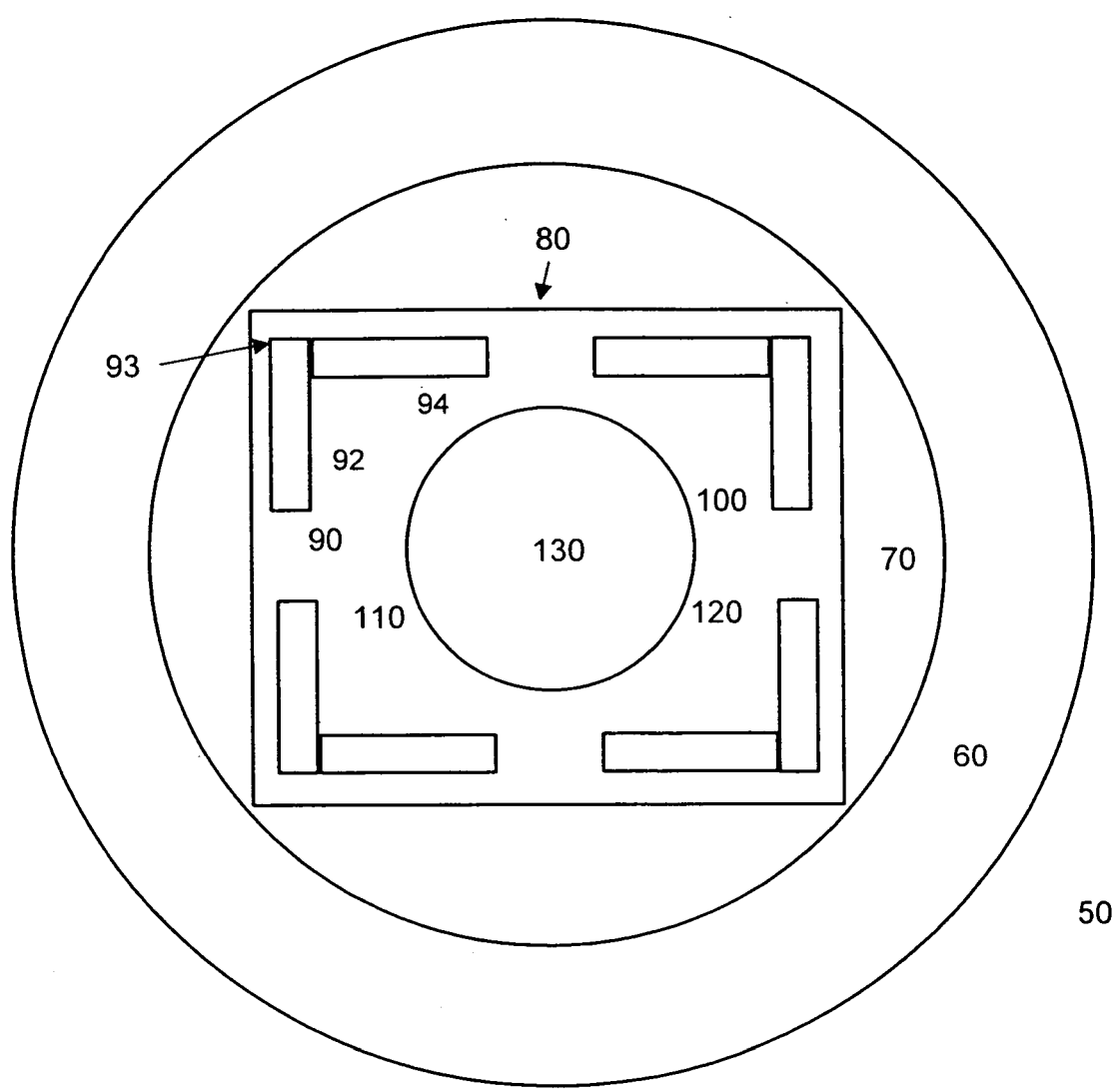
FIG. 3 is a depiction of an image of an iris of an eye in accordance with a preferred embodiment of the present invention.

FIG. 3 is a drawing of an image of eye 50 captured from the image capturing device 40 of FIG. 1.

Referring to FIG. 3, the image of eye 50 comprises a sclera 60, an iris 70, and a pupil 130. As explained earlier, the image 50 is defined by a set of pixel values. Each pixel's intensity value will typically be represented as an eight bit byte, having 256 possible values ranging from 0 to 255. Preferably, a dark frame calibration procedure is performed in step 440 of FIG. 4 by first obtaining an image of an eye with no light directed towards it. The calibration image then produces a reference value for each pixel which is subtracted from any intensities that are subsequently measured for that pixel. Dark frame calibration ensures that each pixel will have a zero intensity at the darkest condition under which an image will be obtained, thereby expanding the useful portion of the 0–255 range. In addition, image stretching can optionally be used to expand the useful range of the eight bit bytes. Image stretching is performed by identifying the maximum and minimum intensity values after dark frame calibration. Each pixel value is then multiplied by the ratio of 255/(maximum intensity−minimum intensity) so that the highest measured intensity has a pixel value of 255 and the lowest pixel value has a pixel value of 0. Image stretching in this fashion is particularly useful for improving the visual appearance of the image.

In step 450, a data set represented by box 80 (FIG. 3) is selected to include iris image 70 but exclude sclera image 60. In a preferred embodiment, sclera image 60 is excluded from the captured image by pre-setting the field of view of image capturing device 40 to a diameter that is less than or equal to an iris diameter that is typical for most subjects. However, other techniques such as threshold detection can be used to determine the location of sclera image 60 and exclude it from box 80.

According to step 460, a number of calculation spaces, 90, 100, 110 and 120 are defined in the iris image 70, each of which corresponds to a particular region of the iris. As shown in FIG. 3, calculation space 90 comprises a first region 92 and a second region 94. The other calculation spaces 100, 110 and 120 similarly comprise their own respective first and second regions. The first and second regions are preferably rectangular in nature and are positioned with respect to one another to create an "L-shaped" calculation space.

The first region 92 and second region 94 are preferably 150 pixels long and 20 pixels wide. First region 92 includes a corner 93 which is preferably placed 17 pixels horizontally and vertically inward of the proximate corner of box 80. Pupil 130 lies within iris 70, and thus, the image of the iris includes the pupil. However, the pupil is not used to calculate the concentration of the optically-active substance and does not lie within the calculation spaces 90, 100, 110 or 120.

As explained earlier, the present invention relates to the discovery that ratios of intensities of polarized light reflected from a subject can be used to predict glucose concentrations. However, it has been found that the ratios vary with glucose concentrations in a periodic manner. It has also been found that light intensity measurements can be subject to "pitch and yaw" errors due to inconsistent alignment of the image capturing device 40, light source 10, and polarizer 20 with respect to the subject's eye 30. This can result in inconsistencies between the images used to generate the pattern match table and those used to measure unknown concentrations. It is theorized that the use of multiple calculation spaces addresses, at least in part, the periodicity of the relationship between intensity ratios and glucose as well as pitch and yaw errors.

Using a predetermined image, in step 470 all of the pixel values in first region 92 are added to obtain a first sum of predetermined intensities, and all of the pixel values in second region 94 are added to obtain a second sum of predetermined intensities. In step 480, the first sum of predetermined intensities is divided by the second sum of predetermined intensities to obtain a predetermined intensity ratio for calculation space 90. The same procedure is then used with remaining calculation spaces 100, 110 and 120 to generate their respective predetermined intensity ratios.

As shown in step 490, the procedure is repeated by obtaining predetermined images that correspond to each of a desired number of known concentrations, and a pattern match table is generated as illustrated in Table 1. The data of Table 1 and the remaining tables herein is provided for the purpose of reference and does not reflect actual data based on experimental results. In addition, the calculation space ratio values shown in the table are multiplied by $10^5$, converting the values into integer representations to improve calculational efficiency when the pattern match table is implemented in a computer.

TABLE 1

Calculation Space Ratios

| | Glucose (mg/dl) | Calculation Space 90 | Calculation Space 100 | Calculation Space 110 | Calculation Space 120 |
|---|---|---|---|---|---|
| 1 | 100 | 101000 | 110000 | 90000 | 112000 |
| 2 | 200 | 130000 | 115000 | 108000 | 117500 |
| 3 | 300 | 145900 | 120000 | 136500 | 127000 |
| 4 | 400 | 200000 | 175000 | 190000 | 183500 |

Preferably, the diameter of the pupil of the subject's eye 30 is maintained at a constant value for each successive predetermined image and known glucose concentration to better ensure that the calculation spaces are consistently located at the same iris position and to reduce variations in light reflection caused by variations in pupil diameter.

Calculation of Unknown Glucose Values

Once the pattern match table has been obtained, unknown concentration values can be determined using the system of FIG. 2. Prior to capturing a measured image of the eye 30, the subject's pupil is preferably adjusted to match its diameter at the time the predetermined images were captured in connection with generating the pattern-match table.

Figure 5:
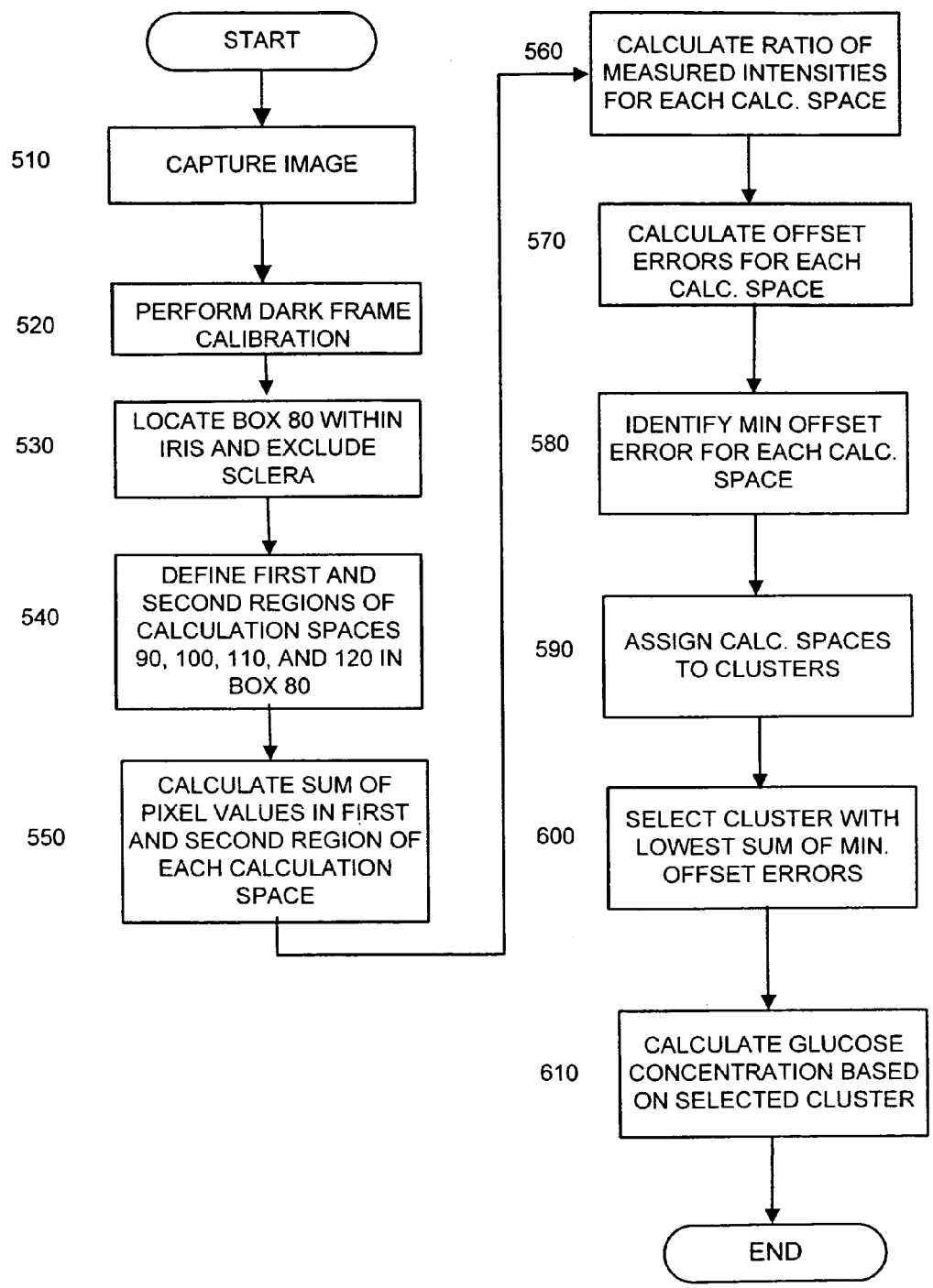
FIG. 5 is a flow chart depicting a method for measuring the concentration of an optically-active substance in accordance with a preferred embodiment of the present invention.

FIG. 5 is a flow chart depicting a method for measuring the concentration of an optically-active substance in accordance with a preferred embodiment of the present invention. According to the method, a measured image such as the one depicted in FIG. 3 is obtained in step 510 in the same way that predetermined images were obtained to generate the pattern-match table. In step 520, dark frame calibration is performed as described previously. As shown in step 530, a data set represented by box 80 is selected to include iris image 70 but exclude sclera image 60.

In step 540, calculation spaces 90, 100, 110 and 120 are defined in the measured image such that they correspond to those used in the predetermined images that were used to generate the pattern-match table.

From the measured image, in step 550 all of the pixels in the first region 92 of calculation space 90 are summed to obtain a first sum of measured light intensity data, and all of the pixels in the second region 94 are summed to obtain a second sum of measured light intensity data. In step 560, the first sum is divided by the second sum to obtain a ratio of measured intensities for calculation space 90. In a similar fashion, ratios of measured intensities are obtained for calculation spaces 90, 100, 110 and 120.

In steps 570 and 580, a minimum offset error is then calculated for each calculation space. As used herein, the term "offset error" refers to the absolute value of the difference between a ratio of measured light intensities and a ratio of predetermined light intensities. To calculate a minimum offset error for each calculation space, the offset errors for each calculation space are first determined by calculating the absolute value of the difference between the measured light intensity ratio for each calculation space and each of the predetermined light intensity ratios in the pattern match table which correspond to the same calculation space.

Table 2 illustrates the calculation of offset errors for calculation space 90. Using the data in Table 1, for example, if the measured light intensity ratio in calculation space 90 were 111000, the offset errors would be as follows:

TABLE 2

| Index of Pattern Match Table Entry | Known Glucose Value (mg/dl) | Predetermined Light Intensity Ratio | Offset Error for Calculation Space 90 |
|---|---|---|---|
| 1 | 100 | 101000 | 10000 |
| 2 | 200 | 130000 | 19000 |
| 3 | 300 | 145900 | 34900 |
| 4 | 400 | 200000 | 99000 |

Thus, for calculation space 90, the minimum offset error is 10000, which corresponds to a known glucose concentration of 100 mg/dl. Note that the predetermined light intensity ratios used to calculate the offset errors are those from the "Calculation Space 90" column in Table 1. In a similar fashion, the offset errors and minimum offset errors are calculated for calculation spaces 100, 110, and 120. Each of the minimum offset errors corresponds to both a calculation space and a known glucose concentration.

According to one embodiment of the present invention, in step 590 a series of clusters or groups are defined, each of which comprises a unique set of calculation spaces or iris regions. The use of clusters provides a means of basing the optically-active substance concentration on those calculation spaces that are the most consistent with one another, thereby filtering out the least consistent calculation space. For example, the clusters can be defined as follows:

Cluster 1: calculation spaces 90 100 and 110

Cluster 2: calculation spaces 100 110 and 120

Cluster 3: calculation spaces 90 100 and 120

Cluster 4: calculation spaces 90 110 and 120

According to this embodiment, in step 600 the minimum offset errors are summed for the calculation spaces comprising each cluster, and the cluster with the lowest minimum offset error sum is identified. The identified cluster will comprise three calculation spaces, each having a minimum offset error that corresponds to a known concentration value in the pattern match table. The three known concentration values are then averaged in step 610 to obtain a measured concentration value for the subject.

For example, if the measured intensity ratio of calculation space 90 were 111000, and the measured intensity ratios of calculation spaces 100, 110 and 120 were 125000, 150000, and 160000, respectively, the following minimum offset errors and corresponding known glucose concentrations would be obtained from the data of Table 1 as follows:

TABLE 3

| Calculation Space | Minimum Offset Error | Known Glucose Concentration Corresponding to Min Offset Error (mg/dl) |
|---|---|---|
| 90 | 10000 | 100 |
| 100 | 5000 | 300 |
| 110 | 13500 | 300 |
| 120 | 23500 | 400 |

The minimum offset error sums for each cluster would then be as follows:

TABLE 4

| Cluster | Calc. Spaces Comprising Cluster | Min. Offset Error Sum |
|---|---|---|
| 1 | 90, 100, 110 | 28500 |
| 2 | 100, 110, 120 | 42000 |
| 3 | 90, 100, 120 | 38500 |
| 4 | 90, 110, 120 | 47000 |

Thus, the cluster having the minimum offset error sum is cluster 1. The calculation spaces comprising cluster 1 have minimum offset errors that correspond to known glucose concentrations of 100, 300, and 300, the average of which is 700/3=233 mg/dl.

Image Rotation

Another aspect of the present invention concerns the optional use of rotated image data to calculate a concentration of an optically-active substance. As explained previously, difficulties in consistently aligning the image capturing device can result in "pitch and yaw" errors, such that the images generated to create the pattern match table are inconsistently aligned with respect to the images used to measure unknown concentrations. According to this aspect of the present invention, a plurality of rotated images are obtained to identify a rotation at which the most consistent results are obtained among the plurality of calculation spaces.

Preferably, rotated image data is generated by capturing one image with the image capturing device and translating the measured light intensity data to correspond to each desired rotation. Techniques for performing such rotational translations are known to those skilled in the art and can be performed by commercially available software packages such as LABVIEW®, a program distributed by National Instruments Corporation of Austin, Tex. It is preferred that the rotations range from about −3° to about +3° with respect to a reference coordinate system. Even more preferably, 60 rotated images are generated at intervals of about 0.1°.

A plurality of calculation spaces, each corresponding to a region of the subject's iris, is defined with respect to the reference coordinate system. Because the calculation spaces remain fixed with respect to the coordinate system, the rotation of the images and associated data translation corresponds to a shift in the measured intensity data that lies within each calculation space. As a result, the measured light intensity ratios for each calculation space will vary with rotational position.

At each rotational position, a minimum offset error is determined for each calculation space in the manner described above. As a result, a number of minimum offset errors will be generated, each of which corresponds to a rotational position, a calculation space, and a known concentration value from the pattern match table. The data can optionally be represented as an array having a number of locations, each of which is defined by a row that corresponds to a rotational position and a column that corresponds to a calculation space. Table 5 depicts a portion of such an array generated for 60 rotated images:

TABLE 5

Minimum Offset Errors

| Rotational Position | Calc. Space 90 | Calc. Space 100 | Calc. Space 110 | Calc. Space 120 |
|---|---|---|---|---|
| −3° | 80000 | 60000 | 50000 | 75000 |
| −2.9° | 81000 | 43000 | 10000 | 1000 |
| −2.8° | 10500 | 9200 | 8100 | 4375 |
| −2.7° | 300 | 2260 | 40000 | 55000 |
| ... | ... | ... | ... | ... |
| 0 | 45000 | 10000 | 16000 | 8200 |
| ... | ... | ... | ... | ... |
| +2.7° | 2268 | 401 | 389 | 16000 |
| +2.8° | 600 | 2970 | 10000 | 2200 |
| +2.9° | 2600 | 4500 | 10500 | 7890 |
| +3.0° | 950 | 1050 | 1000 | 2200 |

As with the example provided above, each minimum offset error corresponds to a known concentration value at which the absolute value of the difference between the measured ratio of light intensities and the predetermined ratios of light intensities in the pattern match table is a minimum.

According to this embodiment, a preferred rotational position is now selected by determining which rotational position has the minimum offset error sum. Using the array structure of Table 5, each row is summed to obtain a minimum offset error sum vector, having a number of rows corresponding to the number of rotated images. Again using the example of Table 5, the following minimum offset error sum vector can be generated as follows:

TABLE 6

| Rotational Position | Min. Offset Error Sum |
|---|---|
| −3° | 265000 |
| −2.9° | 135000 |
| −2.8° | 126675 |
| −2.7° | 97560 |
| ... | ... |
| 0 | 79200 |
| ... | ... |
| +2.7° | 19058 |
| +2.8° | 15770 |
| +2.9° | 25490 |
| +3.0° | 5200 |

Thus, according to the example in Table 6, the minimum offset error sum for the data shown is 5200, indicating that the preferred rotation is +3.0°.

Next, the calculation spaces are grouped into clusters, each comprising a unique subset of the total number of calculation spaces. For purposes of this example, the clusters will again be defined as follows:

Cluster 1: calculation spaces 90 100 and 110
Cluster 2: calculation spaces 100 110 and 120
Cluster 3: calculation spaces 90 100 and 120
Cluster 4: calculation spaces 90 110 and 120

Using the preferred rotation (i.e., the +3° row from Table 5), the minimum offset errors are summed to obtain cluster sums, each comprising the sum of the minimum offset errors for the calculation spaces comprising the cluster. Again, using the example of Table 2, the cluster sums at the selected rotation of +3.0° would be as follows:

Cluster 1 Sum=950+1050+1000=3000
Cluster 2 Sum=1050+1000+2200=4250
Cluster 3 Sum=950+1050+2200=4200
Cluster 4 Sum=950+1000+2200=4150

Thus, cluster 1 has the minimum cluster sum, and is the cluster that would be selected for purposes of calculating the glucose concentration. As explained previously, each minimum offset error corresponds to a predetermined light intensity ratio from Table 1 and a known concentration value from Table 1. Thus, referring back to Table 2, the known concentrations which correspond to the minimum offset errors of 950, 1050 and 1000 for the calculation spaces 90, 100 and 110 are retrieved from the pattern-match table (such as Table 1) and averaged to obtain a glucose concentration.

Windowing Within the Pattern Match Table

As explained earlier, it has been discovered that the ratio of the intensities of light reflected from an iris varies periodically with glucose concentration. It has further been discovered that the period varies with the wavelength of light used. For example, when using a 940 nm light source, one complete cycle is observed in the variation of a measured light intensity ratio as a subject's glucose level is varied from 40–475 mg/dl. When using a 525 nm light source, nearly two cycles are observed over the same glucose range. Without limiting the scope of the invention in any way, this periodicity is theorized to occur because as glucose levels vary, the intensities reflected from the iris vary in a spatially dependent manner. As a result, different iris regions will appear brighter or dimmer as glucose levels are varied. It is believed that because these reflected intensity variations occur over a curved surface—the eye—a periodic relationship is observed.

When a subject's glucose variability is sufficiently narrow, a pattern match table can be constructed for a small range of glucose concentrations, and the periodicity problem can be minimized. However, if the subject's glucose levels vary within a range larger than the period of the intensity ratio versus glucose concentration relationship, it is desirable to employ a technique to account for the periodicity.

Figure 6:
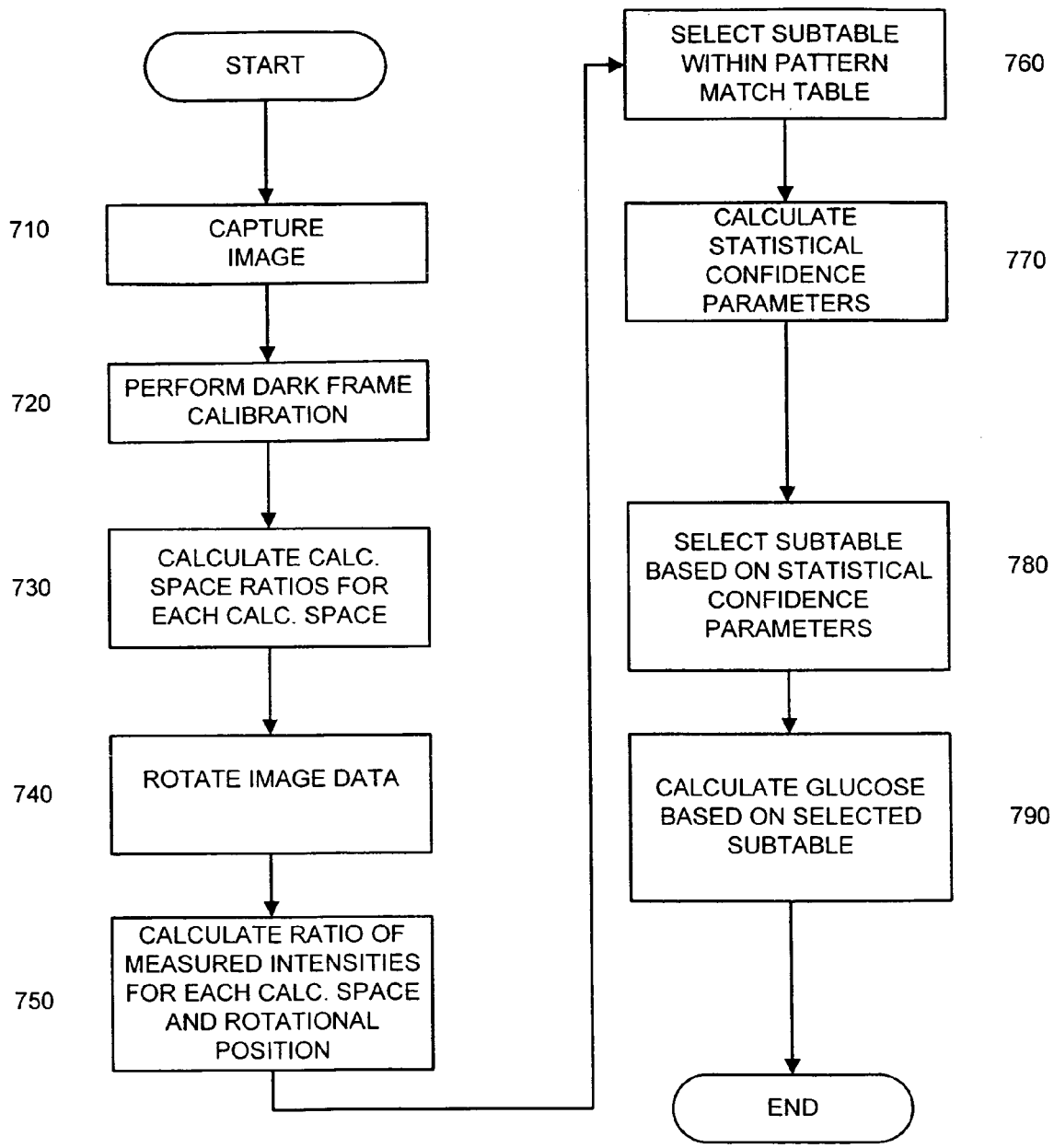
FIG. 6 is a flow chart depicting a method for measuring the concentration of an optically-active substance in accordance with another preferred embodiment of the present invention.

Thus, another optional aspect of the present invention concerns subdividing the pattern-match table into subtables. FIG. 6 is a flow chart depicting a preferred embodiment of a method for calculating the concentration of an optically-active substance using subtables in accordance with a preferred embodiment of the present invention. Referring to the figure, in steps 710–740, rotated image data is generated in the manner previously described. In step 750, a series of ratios of measured light intensities are generated for a number of calculation spaces and rotational positions. In step 760, the pattern-match table is sub-divided into overlapping windows. Using certain statistical confidence parameters, described in detail below, in step 780 one of the windows is selected, and in step 790 the glucose concentration is predicted based on the selected window, instead of based on the entire pattern-match table as a whole.

Table 7 below is an exemplary pattern match table which will be used to demonstrate this aspect of the present invention.

TABLE 7

| | | Calculation Space Ratios | | | |
|---|---|---|---|---|---|
| Index | Glucose (mg/dl) | Calculation Space 90 | Calculation Space 100 | Calculation Space 110 | Calculation Space 120 |
| 1 | 100 | 101000 | 110000 | 90000 | 112000 |
| 2 | 200 | 130000 | 115000 | 108000 | 117500 |
| 3 | 250 | 145900 | 120000 | 136500 | 127000 |
| 4 | 300 | 200000 | 175000 | 190000 | 183500 |
| 5 | 350 | 140000 | 165000 | 120000 | 180000 |
| 6 | 400 | 138000 | 130000 | 115000 | 170000 |

TABLE 7-continued

| | | Calculation Space Ratios | | | |
|---|---|---|---|---|---|
| Index | Glucose (mg/dl) | Calculation Space 90 | Calculation Space 100 | Calculation Space 110 | Calculation Space 120 |
| 7 | 450 | 180000 | 150000 | 160000 | 190000 |
| 8 | 500 | 120000 | 140000 | 125000 | 145000 |

According to this embodiment, a series of subtables, or "windows," is selected from the pattern match table. For larger tables, it is preferred to use three row subtables, while for smaller tables, two row subtables are preferred. It is preferred that the subtables overlap. The use of overlapping subtables is believed to provide a better indication of the quality of the fit or matching between the various calculation spaces and the pattern match table. For purposes of this example, two row, overlapping subtables will be used. Thus, the first subtable comprises rows 1 and 2, the second subtable comprises rows 2 and 3, the third subtable comprises rows 3 and 4, the fourth subtable comprises rows 4 and 5, the fifth subtable comprises rows 5 and 6, the sixth subtable comprises rows 6 7, and the seventh subtable comprises rows 7 and 8.

After capturing an image of the iris, the image is rotated to create a plurality of rotated images as described earlier. At each rotation, a minimum offset error is calculated for each calculation space, but only using the rows of the selected subtable. For example, if at a particular rotation, calculation space 90 had a measured intensity ratio of 195000, then its minimum offset error in the various subtables would be as follows:

Subtable 1: 195000−130000=65000, corresponding to 200 mg/dl of glucose

Subtable 2: 195000−145900=49100, corresponding to 250 mg/dl of glucose

Subtable 3: 200000−195000=5000, corresponding to 300 mg/dl of glucose

Subtable 4: 200000−195000=5000, corresponding to 300 mg/dl of glucose

Subtable 5: 195000−140000=55000, corresponding to 350 mg/dl of glucose

Subtable 6: 195000−180000=15000, corresponding to 450 mg/dl of glucose

Subtable 7: 195000−180000=15000, corresponding to 450 mg/dl of glucose

Using the foregoing technique for each subtable, a minimum offset error is generated for each calculation space at several rotations, preferably 60. As a result of this operation, each subtable will have associated with it an array of minimum offset errors, with each row corresponding to a rotation and each column corresponding to a calculation space. At this point, a preferred rotation is identified in the same manner described previously, except that it is identified based on the subtable of interest only. Thus, within each subtable, the minimum offset errors are summed across all of the calculation spaces at each rotation. The rotation having the minimum offset error sum is identified as the preferred rotation. As a result, each subtable will have a preferred rotation and minimum offset error sum associated with it. This operation is illustrated by the data in Table 8. The rotations may optionally be represented by a rotation index, preferably ranging from −30 to +30:

TABLE 8

| Subtable No. | Beginning Row | Ending Row | Preferred Rotation Index | Minimum Offset Error Sum |
|---|---|---|---|---|
| 1 | 1 | 2 | −2 | 5500 |
| 2 | 2 | 3 | −5 | 6000 |
| 3 | 3 | 4 | +7 | 10000 |
| 4 | 4 | 5 | +15 | 23000 |
| 5 | 5 | 6 | 0 | 15000 |
| 6 | 6 | 7 | −8 | 2200 |
| 7 | 7 | 8 | −3 | 4750 |

Each minimum offset error sum at each preferred rotation index corresponds to a set of minimum offset errors, one for each calculation space. Each calculation space's respective minimum offset error also corresponds to a known concentration value from the pattern match table. Therefore, within each subtable, a glucose number can be calculated at the preferred rotation by identifying the cluster having the lowest cluster error sum and calculating the average of the corresponding known glucose values for the calculation spaces comprising the identified cluster in the manner described above.

Statistical Confidence Parameters

An additional aspect of the present invention involves the use of statistical confidence parameters to identify which subtable as among the several subtables should be selected for purposes of calculating an unknown glucose concentration. Generally speaking, the parameters evaluate the sensitivity of the predicted glucose concentration to the locations of the calculation spaces and to image rotation. Set forth below is a description of several statistical confidence parameters which can be used in various combinations to identify the preferred subtable for calculating a glucose concentration.

The first statistical confidence parameter of interest is called an "Array Deviation." As used herein, "Array Deviation" refers to an array calculated for each subtable according to the following steps:
1. At each rotation, calculate the sum of the minimum offset errors across all calculation spaces, thereby creating a vector of minimum offset error sums. The vector will have a number of values equal to the number of rotations, and each minimum offset error sum will correspond to a rotation and a subtable;
2. Within each vector, calculate the standard deviation of the vector values to obtain a standard deviation that corresponds to the selected subtable.

The foregoing steps are then repeated for each subtable. An array deviation of zero is preferred, and generally indicates that the results for the particular subtable are relatively insensitive to changes in image rotation.

The second statistical confidence parameter of interest is called a "cluster sum deviation." As used herein, the phrase "cluster sum deviation" refers to a variable calculated for each subtable according to the following steps:
1. Identify the preferred rotation for each subtable;
2. Using the rotational image data corresponding to the preferred rotation and the selected subtable, calculate the minimum offset error sum for each cluster by adding the minimum offset errors for the calculation spaces comprising the cluster. This will yield a set of cluster sum values;
3. Calculate the standard deviation of the cluster sum values to obtain a single standard deviation for each subtable.

Preferably, the number of clusters will equal the number of calculation spaces. Thus, if four calculation spaces are used, the standard deviation will be a four point standard deviation based on four cluster sums.

The third statistical confidence parameter of interest is called a "cluster proximity deviation." As used herein, the phrase "cluster proximity deviation," refers to a variable calculated for each subtable according to the following steps:
1. At each rotation, calculate the minimum offset error for each calculation space (as shown in the example of Table 5);
2. For each cluster, calculate the standard deviation of the minimum offset errors for the calculation spaces comprising the cluster. This will yield an array of standard deviations having a number of rows equal to the number of rotational positions and a number of columns equal to the number of clusters;
3. The cluster proximity deviation will equal the lowest standard deviation in the foregoing array.

For example, using the data in Table 5, the standard deviation for cluster 1 at −2.8° is the three point standard deviation of 10500, 9200 and 8100, i.e., 1201. After the procedure is repeated for all clusters and rotations, the lowest standard deviation is selected as the cluster proximity deviation. Cluster proximity deviations are then calculated in the same manner for each subtable.

The next statistical confidence parameter of interest is the "cluster proximity deviation ratio." As used herein, the phrase "cluster proximity deviation ratio" refers to a number that is calculated for each subtable by dividing the subtable's cluster proximity deviation by its cluster sum deviation.

The next statistical confidence parameter of interest is called an "array deviation ratio." As used herein, the phrase "array deviation ratio" refers to a number calculated for each subtable according to the following method:
1. Within each subtable, calculate the minimum offset error for each calculation space at every rotational position to obtain a vector of minimum offset errors for each calculation space, each vector having a number of elements equal to the number of rotational positions;
2. Calculate the standard deviation of the values in each vector to obtain one standard deviation for each calculation space;
3. The array deviation ratio for the subtable of interest will then equal the largest of the foregoing standard deviations divided by the smallest of them.

Using four calculation spaces and 60 rotational positions as an example, step 1 will yield four 60 element vectors of minimum offset errors, one for each of the four calculation spaces. In step 2, the standard deviation of the 60 elements is taken on a vector-by-vector basis, producing four standard deviation values. The array deviation is then calculated by dividing the highest value among the four standard deviations by the lowest value among them. A low array deviation is generally preferred, as it indicates a relatively superior quality of agreement between the various calculation spaces.

The next statistical confidence parameter of interest is called a "dispersion." As used herein, "dispersion" refers to a number calculated for each subtable according to the following method:
1. Using the method described previously, identify the preferred rotation for the subtable of interest;
2. Within each subtable, identify the minimum offset error for each calculation space at the preferred rotation. Each minimum offset error will correspond to a known concentration value in the pattern-match table, and therefore, a row number in the table;

3. Identify the index (i.e., row number) in the pattern match table which corresponds to the identified minimum offset errors for each calculation space;
4. For each cluster of calculation spaces, calculate the standard deviation of the pattern-match table indices that correspond to the minimum offset errors for the calculation spaces comprising the cluster;
5. The lowest of the foregoing standard deviations will be the dispersion.

For example, if at the preferred rotation in a given subtable, calculation space 90 had a minimum offset error corresponding to pattern match table row 2, calculation space 100 had a minimum offset error corresponding to row 3, and calculation spaces 110 and 120 each had minimum offset errors corresponding to row 6, the dispersion would be calculated as shown in Table 9:

TABLE 9

| Cluster | Calculation Spaces Comprising the Cluster | Corresponding Pattern Match Table Indices For the Calculation Spaces | Standard Deviation Of Table Indices |
|---|---|---|---|
| 1 | 90, 100, 110 | 2, 3, 6 | 2.082 |
| 2 | 100, 110, 120 | 3, 6, 6 | 1.732 |
| 3 | 90, 100, 120 | 2, 3, 6 | 2.082 |
| 4 | 90, 110, 120 | 2, 6, 6, | 2.309 |

Thus, in this example, the dispersion would be 1.732. Lower dispersions are preferred, as they generally indicate a relatively superior degree of agreement between the different calculation spaces.

The next statistical confidence parameter of interest is a "proximity Q factor," which is defined by two parameters "Qc" and "Qv." As used herein, the term "Qv" refers to a number calculated for each subtable according to the following method:

1. For each rotational position, identify the calculation space having the lowest minimum offset error. The identified minimum offset error will correspond to a table index in the pattern-match table;
2. Select any one of the clusters which includes the identified calculation space.
3. For each rotational position's selected cluster, calculate a glucose concentration by averaging the known glucose concentrations corresponding to the minimum offset error for each calculation space comprising the cluster. This will yield a vector of glucose concentration values having a number of elements equal to the number of rotational positions;
4. Create a histogram from the data values comprising the foregoing vector and identify the maximum number of vector locations that correspond to any one glucose value. Qv is the identified maximum number of vector locations.

High Qv factor values are preferred, as they indicate that the predicted glucose value is consistent across the rotation space. In addition to the maximum peak, other peaks may be observed in the foregoing histogram and can be assigned to variables $Qv_1$, $Qv_2$, etc. The best rotation orientation fit causes a peak in the histogram, preferably near the 0 degree rotation point. In contrast, multiple peaks during rotation demonstrate ambiguity, and peaks that are off-center (i.e., far from the 0 degree point), indicate an image orientation error relative to the predetermined images used to create the pattern match table.

As mentioned earlier, in addition to Qv, the proximity Q factor comprises another variable, "Qc." As used herein, "Qc" refers to the rotational position at which Qv occurs, based on the histogram generated as described above.

As indicated in step 780 of FIG. 6, the foregoing statistical parameters are used to select a particular subtable from the pattern match table for purposes of calculating a subject's glucose concentration. The parameters can be used in a variety of ways to select the subtable. However, a preferred embodiment for using the parameters is described by the following method:

1. Select the subtables having the two lowest array deviation values;
2. Select the subtable on which to base the glucose calculation by applying the following criteria in the order specified in Table 10:

TABLE 10

| Criterion | Importance | Most Preferred Value |
|---|---|---|
| Cluster Proximity Deviation Ratio | 2 | 1.0 |
| Dispersion | 4 | 0 |
| Qv | 3 | Maximum at center |
| Array Deviation | 1 | Minimum |
| Array Deviation Ratio | 5 | Minimum |
| Minimum Offset Error Sum at Preferred Rotation | 6 | Minimum |

The application of the statistical confidence parameters in accordance with this embodiment is illustrated by the data in Tables 11 and 12:

TABLE 11

| Subtable | Array Deviation | Preferred Rotation Index (−30 to +30) | Min. Offset Error Sum At Pref. Rotation | Cluster Prox. Deviation Ratio |
|---|---|---|---|---|
| 1 | 23230 | 3 | 3662 | 2.01 |
| 2 | 22294 | 3 | 2351 | 1.57 |
| 3 | 22754 | 4 | 8314 | 7.1 |
| 4 | 23486 | 6 | 3171 | 1.87 |
| 5 | 23634 | 6 | 3809 | 2.14 |
| 6 | 24163 | −2 | 4075 | 1.26 |
| 7 | 21567 | 4 | 24618 | 1.61 |

TABLE 12

| Subtable | Array Dev. Ratio | Dispersion | Prox. Q Factor (Qv) | Pred. Glucose (mg/dl) |
|---|---|---|---|---|
| 1 | 3.08 | 0.43 | 48 | 300 |
| 2 | 2.77 | 0.5 | 25 | 317 |
| 3 | 2.81 | 0.43 | 21 | 325 |
| 4 | 2.97 | 0.5 | 39 | 362 |
| 5 | 2.76 | 0 | 26 | 375 |
| 6 | 2.74 | 0.43 | 32 | 404 |
| 7 | 2.92 | 0.5 | 44 | 438 |

According to this embodiment and based on the data of Tables 11 and 12, the two minimum array deviation values occur at subtables 2 and 7. Subtables 2 and 7 have virtually identical cluster proximity deviation ratios of 1.57 and 1.61, respectively. Thus, additional criteria are required to select a subtable. Accordingly, the proximity Q factors are compared next. The Qv of subtable 7 is 44, and the proximity Qv of subtable 2 is 25. Thus, assuming that the Qv values are relatively well centered about the 0 degree rotation point, subtable 7 would be selected for purposes of calculating the glucose concentration.

Having selected subtable 7, it is then used to calculate a glucose concentration based on the cluster having the lowest minimum offset error sum at the preferred rotation, which in this case is +0.3° (corresponding to rotational index 3). As explained earlier, the minimum offset errors are first calculated for each phase, but they are based only on the data in subtable 7. The minimum offset errors are then summed for each cluster, and the cluster having the lowest minimum offset error sum is selected. The known glucose values from subtable 7 (not shown) which correspond to the minimum offset errors for the calculations spaces comprising the selected cluster are then averaged to obtain the final glucose concentration, which in the example of Table 12 is 438 mg/dl.

Use of Multiple wavelength Light Sources

In accordance with another preferred embodiment of the present invention, glucose calculations are made using images generated by a variety of different wavelengths of light. As explained earlier, the ratios of intensities of light reflected from an iris vary periodically with glucose concentrations. As a result, over a range of concentrations, the same intensity ratio may correspond to a number of different concentrations. The use of images generated by multiple wavelengths of light provides an additional means of addressing the periodicity issue.

In accordance with this embodiment, light source 10 of FIG. 1 is adapted to transmit light at a plurality of different wavelengths. Alternately, a plurality of different light sources can be used to generate different images at different wavelengths. It is preferred to generate images using red (625 nm), green (525 nm) and near infrared (940 nm).

The period of reflected light intensity ratios versus glucose concentration is a function of the light's wavelength. By using a variety of images generated by different wavelengths of light, the periodicity problem can be eliminated because any actual glucose number must satisfy the relationships between intensity ratio and glucose concentration for all wavelengths that are used. Thus, while the intensity ratio measured for a given wavelength may correspond to a number of different glucose concentrations, only one of those concentrations will correspond to the intensities measured for the other wavelengths. Thus, the periodicity problem can be minimized and a unique predicted glucose concentration can be obtained.

In accordance with this embodiment, after pattern match tables are generated at each different wavelength, measured images are generated using the corresponding wavelengths. Using the corresponding measured images and pattern match tables, glucose concentrations are calculated using the methods described above. Once a glucose concentration has been calculated based on each wavelength, the results are averaged to obtain a final predicted glucose concentration.

The foregoing embodiments are merely examples of the present invention. Those skilled in the art may make numerous uses of, and departures from, such embodiments without departing from the spirit and the scope of the present invention. Accordingly, the scope of the present invention is not to be limited to or defined by such embodiments in any way, but rather, is defined solely by the following claims.

What is claimed is:

1. An apparatus, comprising:
   a. a light source adapted to transmit light towards an object containing a solution of an optically-active substance;
   b. a polarizer, positioned between said light source and said object;
   c. a first image capturing device, positioned to receive a portion of light reflected from said object and adapted to create a measured image therefrom, said measured image defining measured light intensity data;
   d. a processor; and
   e. a database, said database comprising predetermined concentration data for said optically-active substance and predetermined light intensity data, wherein said processor is further configured to calculate a concentration of said optically-active substance based on a selected portion of said measured light intensity data, a selected portion of said predetermined concentration data, and a selected portion of said predetermined light intensity data;
   wherein said predetermined concentration data comprises one or more known concentration values and said predetermined light intensity data comprises one or more predetermined calculation space ratios.

2. The apparatus of claim 1, wherein said object is a human eye having an iris and said measured image comprises a measured image of said iris.

3. The apparatus of claim 1, further comprising a housing, wherein the light source, polarizer, first image capturing device and processor are contained in the housing.

4. The apparatus of claim 3, wherein the apparatus is a hand-held device.

5. The apparatus of claim 3, wherein the apparatus is a portable device.

6. The apparatus of claim 1, wherein said optically-active substance is glucose.

7. The apparatus of claim 1, further comprising a memory, wherein said database is stored in said memory.

8. The apparatus of claim 1 wherein said object is a human eye having an iris and said polarizer is positioned to transmit light from said light source towards said iris such that said transmitted light contacts said iris at one or more angles of incidence, thereby creating said portion of light reflected from said object.

9. The apparatus of claim 8, wherein at least one of said one or more angles of incidence is sufficient to cause polarization.

10. The apparatus of claim 8, wherein at least one of said one or more angles of incidence is Brewster's angle.

11. The apparatus of claim 1, wherein said image capturing device is a charge coupled device.

12. The apparatus of claim 1, wherein said first image capturing device comprises a plurality of locations, said first image capturing device is adapted to measure the intensity of light received at each said location, thereby creating one or more measured intensities of said portion of light reflected from said object, and said processor is adapted to receive said one or more measured intensities of said portion of light reflected from said object, wherein said measured light intensity data comprises said one or more measured intensities of light reflected from said object.

13. The apparatus of claim 12, wherein said one or more measured intensities of light reflected from said object defines an array having one or more calculation spaces defined therein, each said calculation space having a plurality of measured light intensities defined therein, and wherein said selected portion of said measured light intensity data comprises at least one of said pluralities of measured light intensities in said one or more calculation spaces.

14. The apparatus of claim 13, wherein said processor is configured to calculate a calculation space ratio corresponding to each said calculation space, wherein said selected portion of said measured light intensity data comprises at least one of said calculation space ratios.

15. The apparatus of claim 14, wherein each said calculation space ratio comprises a ratio of measured light intensities in the corresponding calculation space.

16. The apparatus of claim 14, wherein said processor is further configured to calculate a first and second sum of measured light intensities in each said calculation space, wherein each said calculation space ratio comprises a ratio of said corresponding first sum and said corresponding second sum.

17. The apparatus of claim 16, wherein each said calculation space has a first length and a first width defining a first region therein and a second length and a second width defining a second region therein, wherein each said first sum comprises a sum of the measured light intensities in each said corresponding first region of said corresponding calculation space, and each said second sum comprises a sum of the measured light intensities in each said corresponding second region of said corresponding calculation space.

18. The apparatus of claim 13, wherein said one or more calculation spaces is four calculation spaces.

19. The apparatus of claim 13, wherein said one or more calculation spaces is two calculation spaces.

20. The apparatus of claim 1, wherein each said predetermined calculation space ratio comprises a predetermined ratio of light intensities, each said predetermined ratio of light intensities corresponds to a predetermined calculation space defined in an array of predetermined light intensities, and wherein each said predetermined light intensity in said array comprises an intensity of light measured at one of a plurality of locations defined by a second image capturing device.

21. The apparatus of claim 20, wherein said first image capturing device and said second image capturing device are the same device.

22. The apparatus of claim 20, wherein each said predetermined ratio of light intensities comprises a ratio of a first sum of said predetermined light intensities and a second sum of said predetermined light intensities, wherein both said first sum and said second sum correspond to the same predetermined calculation space to which said predetermined ratio of light intensities corresponds.

23. The apparatus of claim 22, wherein each said predetermined calculation space comprises a first region having a first length and a first width and a second region having a second length and a second width, wherein each said first sum of predetermined light intensities comprises a sum of the predetermined light intensities in each said first region and each said second sum comprises a sum of the predetermined light intensities in each said second region.

24. The apparatus of claim 1, wherein said object comprises a plurality of object regions, said predetermined concentration data comprises two or more known concentration values of said optically-active substance, and said predetermined light intensity data comprises a plurality of predetermined ratios of light intensities, each said predetermined ratio of light intensities corresponding to both one of said object regions and one of said known concentration values.

25. The apparatus of claim 24, wherein said object is an eye having an iris.

26. The apparatus of claim 24, wherein said light source and said polarizer are positioned to transmit light from said light source towards said plurality of object regions, such that said transmitted light contacts said plurality of object regions at one or more angles of incidence, thereby creating said portion of light reflected from said object, and said processor is configured to calculate at least one measured ratio of light intensities corresponding to each said object region from said portion of light reflected from said object.

27. The apparatus of claim 26, wherein at least one of said angles of incidence is sufficient to cause polarization.

28. The apparatus of claim 26, wherein at least one of said angles of incidence is Brewster's angle.

29. The apparatus of claim 1, wherein said processor is configured to generate an offset error array.

30. The apparatus of claim 29, wherein said offset error array comprises a plurality of offset errors, each said offset error having an offset error array location defined by a row that corresponds to a known concentration of said optically-active substance and a column that corresponds to one of a plurality of iris regions of an eye.

31. The apparatus of claim 30, wherein each said offset error comprises the absolute value of the difference between a measured light intensity ratio and a predetermined light, intensity ratio, wherein both said measured light intensity ratio and said predetermined light intensity ratio correspond to the same iris region to which said offset error corresponds.

32. The apparatus of claim 31, wherein said processor is further configured to calculate a minimum offset error array.

33. The apparatus of claim 32, wherein said minimum offset error array comprises a plurality of minimum offset errors, each said minimum offset error corresponding to a row and a column of said offset error array, each said minimum offset error comprising the lowest offset error in the corresponding column of said offset error array such that each minimum offset error corresponds to one of said known concentration values and one of said iris regions.

34. The apparatus of claim 33, wherein said processor is further configured to calculate a cluster offset error sum for one or more clusters, each said cluster comprising a set of iris regions in said plurality of iris regions, each said cluster offset error sum comprising the sum of the minimum offset errors for each iris region comprising the cluster.

35. The apparatus of claim 34, wherein said processor is further configured to calculate a concentration of said optically-active substance by: (i) selecting the cluster having the minimum cluster offset error sum among said one or more clusters, and (ii) averaging the known concentration values corresponding to the minimum offset errors for the iris regions comprising the selected cluster.

36. The apparatus of claim 1, wherein said light source is adapted to transmit light at a plurality of selected wavelengths.

37. The apparatus of claim 1, wherein said apparatus comprises a plurality of light sources, each of which is adapted to transmit light at one or more selected wavelengths.

38. The apparatus of claim 1, wherein said object is a human eye having an iris and a pupil within said iris, said iris comprising a plurality of iris regions, and said measured image comprises a measured image of said iris and a measured image of said pupil.

39. The apparatus of claim 38, wherein said plurality of iris regions comprises three or more iris regions.

40. The apparatus of claim 39, wherein said processor is adapted to calculate a plurality of measured light intensity ratios from said measured light intensity data, each said measured light intensity ratio corresponding to one of said plurality of iris regions, and wherein said selected portion of said measured light intensity data comprises at least one of said measured light intensity ratios.

41. The apparatus of claim 38, wherein said plurality of iris regions comprises four iris regions, each corresponding to an iris image region in said measured image of said iris, said four iris image regions defining first and second pairs of iris image regions, wherein each said pair of iris image regions defines a line through said pupil image.

42. The apparatus of claim 38, wherein each said iris region comprises a first and second rectangular regions, wherein each said first rectangular region defines first rectangular region measured light intensity data and wherein each said second rectangular region defines second rectangular region measured light intensity data, said processor is further configured to calculate a first sum of said first rectangular region measured light intensity data and a second sum of said second rectangular region measured light intensity data, and wherein each said measured light intensity ratio comprises a ratio of the first sum and the second sum corresponding to the same iris region to which said measured light intensity ratio corresponds.

43. The apparatus of claim 38, said apparatus further comprising a database operatively coupled to said processor, said database including an array of predetermined light intensity ratios, said array comprising a plurality of array locations, each said array location being defined by a row corresponding to a known concentration value for said optically-active substance and a column corresponding to one of said plurality of iris regions.

44. The apparatus of claim 43, wherein said processor is further configured to calculate a concentration of said optically-active substance according to the following method:
   a. subdividing said array into a plurality of sub-arrays;
   b. selecting a subarray based on at least one statistical confidence parameter;
   c. defining a plurality of clusters, each said cluster comprising a set of iris regions from said plurality of iris regions;
   d. selecting one of said plurality of clusters; and
   e. calculating said concentration of an optically-active substance based on said selected cluster, said selected subarray and said measured light intensity data.

45. The apparatus of claim 43, wherein said at least one statistical confidence parameter is selected from the group consisting of an array deviation, a cluster sum deviation, a cluster proximity deviation, a cluster proximity deviation ratio, an array deviation ratio, a minimum offset error sum, a dispersion and a proximity Q factor.

46. The apparatus of claim 43, wherein said processor is further configured to calculate an offset error array.

47. The apparatus of claim 46, wherein said processor is adapted to calculate a plurality of measured light intensity ratios from said measured light intensity data, each said measured light intensity ratio corresponding to one of said iris regions, said offset error array comprises a plurality of offset error array locations, each said offset error array location being defined by a row that corresponds to one of said known concentration values and a column that corresponds to one of said iris regions.

48. The apparatus of claim 47, wherein each said offset error in said offset error array is generated according to the following steps:
   a. selecting a known concentration value corresponding to one of said rows in said selected subarray;
   b. selecting one of said iris regions; and
   c. calculating the absolute value of the difference between the measured light intensity ratio corresponding to the selected iris region and the predetermined light intensity ratio corresponding to both the selected iris region and the selected known concentration value.

49. The apparatus of claim 47, wherein said processor is further configured to calculate a minimum offset error corresponding to each said iris region in said plurality of iris regions.

50. The apparatus of claim 49, wherein each said minimum offset error comprises the lowest offset error in the column of the offset error array which corresponds to the same iris region to which the minimum offset error corresponds.

51. The apparatus of claim 50, wherein said processor is further configured to calculate a cluster minimum offset error sum for each said cluster in said plurality of clusters.

52. The apparatus of claim 51, wherein each said cluster minimum offset error sum comprises the sum of the minimum offset errors for the iris regions comprising the cluster.

53. The apparatus of claim 52, wherein said step of selecting one of said plurality of clusters comprises selecting the cluster having the lowest cluster minimum offset error sum.

54. The apparatus of claim 53, wherein said step of calculating a concentration of said optically-active substance comprises averaging the known concentration values corresponding to the minimum offset errors of the iris regions comprising the selected cluster.

55. The apparatus of claim 1, wherein said processor is further configured to generate a plurality of rotated images from said measured image, thereby creating rotated image data, and wherein said processor is configured to calculate said concentration of said optically-active substance based on said rotated image data and said selected portion of measured light intensity data.

56. A method of calculating a concentration of an optically-active substance in an object containing a solution of said optically-active substance, the method comprising the steps of:
   a. providing at least one measured image of said object, each said measured image defining an array of measured intensities of light reflected from said object;
   b. calculating at least one ratio of measured light intensities from said array of measured intensities of light reflected from said object;
   c. calculating a concentration of said optically-active substance based on said at least one ratio of measured intensities, wherein calculating said concentration of said optically-active substance based on said at least one ratio of measured intensities comprises: (1) defining a plurality of calculation spaces in said measured image, each said calculation space defining a plurality of measured intensities of light; and (2) calculating a calculation space ratio in each said calculation space, wherein said at least one ratio of measured light intensities comprises at least one of said calculation space ratios; and
   d. displaying said calculated concentration.

57. The method of claim 56, wherein said object is a human eye having an iris.

58. The method of claim 56, wherein said step of calculating a calculation space ratio in each said calculation space comprises:
   a. defining first and second regions in each said calculation space, wherein said first region defines a first region of measured light intensities and said second region defines a second region of measured light intensities;
   b. calculating a sum of measured light intensities in said first region, thereby creating a first sum;
   c. calculating a sum of measured light intensities in said second region, thereby creating a second sum; and
   d. calculating a ratio of said first sum and said second sum.

59. The method of claim 56, wherein said plurality of calculation spaces comprises three or more calculation spaces.

60. The method of claim 56, wherein said plurality of calculation spaces comprises four calculation spaces.

61. The method of claim 60, wherein said measured image of an object comprises a measured image of an iris and a pupil, said four calculation spaces define first and second pairs of calculation spaces, and wherein each said pair of calculation spaces defines a line passing through said pupil image.

62. The method of claim 61, wherein each said first region of each said calculation space and each said second region of each said calculation space are rectangular in shape and positioned adjacent with respect to one another.

63. The method of claim 61, wherein each said first region of each said calculation space and each said second region of each said calculation space form an L-shape.

64. The method of claim 56, further comprising:
   a. providing a plurality of predetermined images of a reference object, each said predetermined image corresponding to a known concentration of said optically-active substance and defining an array of predetermined intensities of light reflected from said object; and
   b. calculating at least one predetermined ratio of intensities within each said array of predetermined intensities of light reflected from said reference object;
   wherein said step of calculating a concentration of said optically-active substance comprises calculating a concentration of said optically-active substance based on said at least one ratio of measured intensities and said at least one predetermined ratio of intensities within each said array of predetermined intensities of light reflected from said reference object.

65. The method of claim 64, wherein said reference object is said object.

66. The method of claim 64, wherein said step of calculating at least one predetermined light intensity ratio within each said array of predetermined intensities of light reflected from said reference object comprises:
   a. defining at least one predetermined calculation space in each said predetermined image; and
   b. calculating a predetermined calculation space ratio in each said predetermined calculation space, wherein said at least one predetermined light intensity ratio comprises at least one of said predetermined calculation space ratios.

67. The method of claim 66, wherein said step of calculating a predetermined calculation space ratio in each said calculation space comprises:
   a. defining a first predetermined region and a second predetermined region in each said predetermined calculation space, wherein said first predetermined region defines a first predetermined region of predetermined light intensities and said second predetermined region defines a second predetermined region of predetermined light intensities;
   b. calculating a sum of predetermined intensities in said first predetermined region, thereby creating a first predetermined sum;
   c. calculating a sum of predetermined intensities in said second predetermined region, thereby creating a second predetermined sum; and
   d. calculating a ratio of said first predetermined sum and said second predetermined sum.

68. The method of claim 67, wherein said at least one predetermined calculation space comprises three or more calculation spaces.

69. The method of claim 67, wherein said at least one predetermined calculation spaces comprises four calculation spaces.

70. The method of claim 56, further comprising generating an offset error array.

71. The method of claim 70, wherein said offset error array comprises a plurality of offset errors, each said offset error having an offset error array location defined by a row that corresponds to one of a plurality of known concentration values of said optically-active substance and a column that corresponds to one of a plurality of iris regions of an eye.

72. The method of claim 71, wherein said offset error array comprises the absolute value of the difference between one of said at least one ratio of measured intensities and a predetermined light intensity ratio, wherein both said one of said at least one ratio of measured intensities and said predetermined light intensity ratio correspond to the same iris region to which said offset error corresponds.

73. The method of claim 72, further comprising generating a minimum offset error array.

74. The method of claim 73, wherein said minimum offset error array comprises a plurality of minimum offset errors, each said minimum offset error corresponding to a row and a column of said offset error array, each said minimum offset error comprising the lowest offset error in the corresponding column of said offset error array, whereby each said minimum offset error corresponds to one of said known concentration values and one of said iris regions.

75. The method of claim 74, further comprising:
   a. defining a plurality of clusters, wherein each said cluster comprises a set of said iris regions;
   b. calculating a sum of the minimum offset errors for the set of iris regions comprising each cluster;
   c. selecting the cluster having the lowest sum of the minimum offset errors; and
   d. averaging the known concentration values which correspond to the minimum offset errors for each iris region comprising the selected cluster.

76. The method of claim 56 wherein said at least one measured image of said object comprises a plurality of measured images, each said measured image corresponding to a different wavelength of light reflected from said object.

77. A method of calculating a concentration of an optically-active substance in an object containing a solution of said optically-active substance, the method comprising:
   a. providing a measured image of said object, said measured image defining an array of measured intensities of light reflected from said object;
   b. rotating said measured image to a plurality of rotational positions, wherein said plurality of rotational positions comprises 60 rotational positions, thereby generating a plurality of rotated measured intensities of light reflected from said object;

c. calculating a concentration of said optically-active substance based on said measured intensities of light reflected from said object and said rotated measured intensities of light reflected from said object; and d. displaying said calculated concentration.

78. The method of claim 77, wherein said rotational positions are spaced apart from one another by about 0.1 degree.

79. The method of claim 77, wherein said plurality of rotated positions define a range of values from about −3.0 degrees to about +3.0 degrees with respect to said measured image.

80. The method of claim 77 wherein said object is a human eye.

81. A method of calculating a concentration of an optically-active substance in an object containing a solution of said optically-active substance, said object including a plurality of object regions, the method comprising:

a. providing a plurality of measured intensity values of light reflected from said object, each said measured intensity value corresponding to one of said object regions;

b. providing a plurality of predetermined intensities of light reflected from a reference object containing a solution of said optically-active substance, said reference object including a plurality of reference object regions, and each said predetermined intensity of light corresponding to one of said reference object regions and to a known concentration of said optically-active substance;

c. selecting a portion of said plurality of predetermined intensities of light reflected from a reference object based on one or more statistical confidence parameters;

d. calculating a concentration of said optically-active substance in said object based on one or more of said measured intensities of light reflected from said object and said selected portion of said plurality of predetermined intensities of light reflected from a reference object; and e. displaying said calculated concentration.

82. The method of claim 81, wherein said one or more statistical confidence parameters are selected from the group consisting of an array deviation, a cluster sum deviation, a cluster proximity deviation, an array deviation ratio, a cluster proximity deviation ratio, a dispersion, a proximity Q factor, and a minimum offset error sum.

83. The method of claim 81, wherein said object is a human eye.

84. The method of claim 81, wherein the reference object is the same as said object.

85. The method of claim 81, wherein said measured intensities of light reflected from said object correspond to a plurality of wavelengths of light.

86. A method of calculating the concentration of an optically-active substance in an object containing a solution of said substance, the method comprising:

a. providing a measured image of said object, said measured image defining measured light intensity data;

b. providing a plurality of predetermined images of a reference object containing a solution of said optically-active substance, each said predetermined image corresponding to a known concentration of said optically-active substance, said plurality of predetermined images defining an array of predetermined light intensity data, said array of predetermined light intensity data further defining a plurality of subarrays of predetermined light intensity data;

c. rotating said measured image to a plurality of rotational positions, thereby generating rotated light intensity data;

d. selecting one of said subarrays of predetermined light intensity data;

e. calculating the concentration of said optically-active substance in said object based on said measured light intensity data, said rotated light intensity data and said selected subarray of predetermined light intensity data; and f. displaying said calculated concentration.

87. The method of claim 86, wherein said plurality of rotational positions comprises 60 rotational positions.

88. The method of claim 86, wherein said plurality of rotational positions range from about −3 degrees to about +3 degrees from the orientation of the measured image.

89. The method of claim 86, wherein said plurality of rotational positions are spaced apart in increments of about 0.1 degree.

90. The method of claim 86, wherein said step of selecting a subarray is based on one or more statistical confidence parameters.

91. The method of claim 90, wherein said statistical confidence parameters are selected from the group consisting of an array deviation, a cluster sum deviation, a cluster proximity deviation, an array deviation ratio, a cluster proximity deviation ratio, a dispersion, a proximity Q factor, and a minimum offset error.

92. The method of claim 86, further comprising calculating an offset error array based on said measured light intensity data.

93. The method of claim 92, wherein said object comprises a plurality of object regions and said offset error array comprises a plurality of offset errors, each said offset error corresponding to one of said object regions.

94. The method of claim 93, wherein said plurality of object regions is two or more object regions.

95. The method of claim 93, wherein said plurality of object regions is four object regions.

96. The method of claim 95, wherein each said object region comprises first and second subregions, and wherein each said first subregion and second subregion are positioned with respect to one another such that they form an L-shape.

97. The method of claim 93, wherein said measured light intensity data comprises a plurality of measured light intensity values and said array of predetermined light intensity data comprises a plurality of predetermined light intensity values, and wherein each said offset error comprises the difference between a selected ratio of measured light intensity values from said plurality of measured light intensity values and a selected ratio of predetermined light intensity values from said selected plurality of predetermined light intensity values.

98. The method of claim 93, further comprising calculating at least one minimum offset error based on said offset error array, each said minimum offset error corresponding to one of said object regions and one of said known concentration values of said optically-active substance.

99. The method of claim 98, further comprising defining a plurality of clusters, each said cluster comprising a set of object regions, and selecting one of said clusters, wherein said step of calculating the concentration of said optically-active substance is further based on said selected cluster.

100. The method of claim 99, wherein said step of selecting one of said clusters comprises calculating the sum of the minimum offset errors for each of the object regions comprising each cluster and selecting the cluster having the lowest sum of the minimum offset errors.

101. The method of claim 100, wherein said step of calculating the concentration of said optically-active substance comprises averaging the known concentration values corresponding to the minimum offset errors of each of the object regions comprising the selected cluster.

102. The method of claim 86 wherein said object is an eye.

103. The method of claim 86, wherein said optically-active substance is glucose.

104. The method of claim 86, wherein said reference object is the same as said object.

105. A computer readable medium comprising instructions for calculating the concentration of an optically-active substance in an object containing a solution of said substance, the instructions comprising:
   a. receiving a measured image of said object, said measured image defining measured light intensity data;
   b. receiving a plurality of predetermined images of a reference object containing a solution of said optically-active substance, each said predetermined image corresponding to a known concentration of said optically-active substance, said plurality of predetermined images defining an array of predetermined light intensity data, said array of predetermined light intensity data further defining a plurality of subarrays of predetermined light intensity data;
   c. rotating said measured image to a plurality of rotational positions, thereby generating rotated light intensity data;
   d. selecting one of said subarrays of predetermined light intensity data; and
   e. calculating the concentration of said optically-active substance in said object based on said measured light intensity data, said rotated light intensity data and said selected subarray of predetermined light intensity data.

106. An apparatus for calculating the concentration of an optically-active substance based on light reflected from an object containing a solution of said substance, the apparatus comprising:
   a. a memory comprising predetermined concentration data and predetermined light intensity data;
   b. means for capturing measured light intensity data for light reflected from said object; and
   c. means for calculating a concentration of said optically-active substance based on said measured light intensity data, said predetermined concentration data and said predetermined light intensity data.

107. The apparatus of claim 106, further comprising a means for generating rotated image data.

108. The apparatus of claim 106, further comprising a means for selecting a portion of said predetermined concentration data based on one or more statistical confidence parameters.

109. The apparatus of claim 106, wherein said measured light intensity data corresponds to one or more wavelengths of light.

* * * * *